US010772888B2

(12) United States Patent
Mahjour et al.

(10) Patent No.: US 10,772,888 B2
(45) Date of Patent: Sep. 15, 2020

(54) SOLID PHARMACEUTICAL COMPOSITIONS CONTAINING AN INTEGRASE INHIBITOR

(71) Applicant: MERCK SHARP & DOHME CORP., Rahway, NJ (US)

(72) Inventors: Majid Mahjour, Schwenksville, PA (US); Feng Li, Dresher, PA (US); Decheng Ma, Souderton, PA (US); Sutthilug Sotthivirat, Lansdale, PA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 526 days.

(21) Appl. No.: 15/483,030

(22) Filed: Apr. 10, 2017

(65) Prior Publication Data

US 2017/0231993 A1 Aug. 17, 2017

Related U.S. Application Data

(62) Division of application No. 13/503,939, filed as application No. PCT/US2010/053507 on Oct. 21, 2010, now Pat. No. 9,649,311.

(60) Provisional application No. 61/254,869, filed on Oct. 26, 2009.

(51) Int. Cl.
*A61K 31/513* (2006.01)
*A61K 9/20* (2006.01)
*A61K 31/506* (2006.01)
*A61K 45/06* (2006.01)
*A61K 9/24* (2006.01)

(52) U.S. Cl.
CPC .......... *A61K 31/513* (2013.01); *A61K 9/2009* (2013.01); *A61K 9/2013* (2013.01); *A61K 9/2054* (2013.01); *A61K 9/2077* (2013.01); *A61K 9/2095* (2013.01); *A61K 31/506* (2013.01); *A61K 45/06* (2013.01); *A61K 9/209* (2013.01)

(58) Field of Classification Search
None
See application file for complete search history.

(56) References Cited

U.S. PATENT DOCUMENTS

| | | | |
|---|---|---|---|
| 6,087,383 A | 7/2000 | Singh et al. | |
| 6,352,720 B1 | 3/2002 | Martin et al. | |
| 6,369,094 B1 | 4/2002 | Bentley et al. | |
| 7,169,780 B2 | 1/2007 | Crescenzi et al. | |
| 7,217,713 B2 | 5/2007 | Crescenzi et al. | |
| 7,232,819 B2 | 6/2007 | Di Francesco et al. | |
| 7,414,045 B2 | 8/2008 | Crescenzi et al. | |
| 7,435,734 B2 | 10/2008 | Crescenzi et al. | |
| 7,459,452 B2 | 12/2008 | Di Francesco et al. | |
| 7,687,509 B2 | 3/2010 | Haberson | |
| 7,754,731 B2 | 7/2010 | Belyk et al. | |
| 2005/0075356 A1 | 4/2005 | Di Francesco et al. | |
| 2005/0256202 A1 | 11/2005 | Kim et al. | |
| 2006/0046985 A1 | 3/2006 | Crescenzi et al. | |
| 2006/0122205 A1 | 6/2006 | Belyk et al. | |
| 2007/0259894 A1 | 11/2007 | Kassahun | |
| 2007/0292504 A1 | 12/2007 | Pourkavoos | |
| 2008/0118559 A1 | 5/2008 | Cruanes et al. | |
| 2008/0176869 A1 | 7/2008 | Crescenzi et al. | |
| 2008/0275004 A1 | 11/2008 | Crescenzi et al. | |
| 2010/0204292 A1 | 12/2010 | Aurora et al. | |

FOREIGN PATENT DOCUMENTS

| | | |
|---|---|---|
| WO | 1992019227 A2 | 11/1992 |
| WO | 2001038332 A1 | 11/2000 |
| WO | 2002030930 A2 | 4/2002 |
| WO | 2003035077 A1 | 5/2003 |
| WO | 2003086319 A2 | 10/2003 |
| WO | 2004058756 A1 | 7/2004 |
| WO | 2005065656 A2 | 7/2005 |
| WO | 2006060681 A2 | 6/2006 |
| WO | 2006060711 A2 | 6/2006 |
| WO | 2006060731 A2 | 6/2006 |
| WO | 2007087188 A2 | 8/2007 |
| WO | 2008043167 A1 | 4/2008 |
| WO | 2009002823 A2 | 12/2008 |
| WO | 2009054743 A1 | 4/2009 |

(Continued)

OTHER PUBLICATIONS

Carter, John C., "The Role of Disintegrants in Solid Oral Dosage Manufacturing", Carter Pharmaceutical Consulting, Inc., 2002-2008, pp. 1-3.
FMC BioPlymer, "Avicel DG Binder: A superior excipient for roller compaction and dry granulation", Oct. 29, 2009, p. 2, para 3-4; p. 5, para 1.
Kumprakob, Usanee, et al., "Permeation Enhancement of Ketoprofen Using a Supersaturated System with Antinucleant Polymers", Bio. Pharm. Bulletin, 2005, pp. 1684-1688, vol. 28, No. 9.
Yeoh, Thean Y., "Use of Polymer Additives to Inhibit Phenytoin Nucleation and Crystal Growth From Supersaturated Aqueous Solution", Abstract of Ph.D. Thesis, Purdue University, 1994.
Kibbe, A., et al., "Hydroxypropyl Methylcellulose", Handbook of Pharmaceutical Excipients, 2000, pp. 252-255, American Pharmaceutical Association, Washington, DC.

(Continued)

*Primary Examiner* — Tigabu Kassa
(74) *Attorney, Agent, or Firm* — Nicole M. Beeler; John C. Todaro

(57) ABSTRACT

Compressed tablets for oral administration containing raltegravir in the form of a pharmaceutically acceptable salt are described. The tablets comprise:
(A) an intragranular component comprising (i) an effective amount of an alkali metal salt of raltegravir, (ii) optionally a first superdisintegrant, and (iii) a binder; and
(B) an extragranular component comprising (i) a second superdisintegrant, (ii) a filler, and (iii) a lubricant. Methods for preparing the tablets and the use of the tablets, optionally in combination with other anti-HIV agents, for the inhibition of HIV integrase, for the treatment or prophylaxis of HIV infection, or for the treatment, delay in the onset, or prophylaxis of AIDS are also described.

16 Claims, 1 Drawing Sheet

(56) References Cited

FOREIGN PATENT DOCUMENTS

WO        2011053504 A1      5/2011

OTHER PUBLICATIONS

Kibbe, A., "Poloxamer", Handbook of Pharmaceutical Excipients, 2000, pp. 252-255, American Pharmaceutical Association, Washington, DC.

Gusstafsson, et al., "Characterisation of particle properties and compaction behavior of hydroxypropyl methylcellulose with different degrees of methoxy/hydroxypropyl substitution", European Journal of Pharmaceutical Sciences, 1999, pp. 171-184, vol. 9.

Hussain, et al., "A thermoheological investigation into the gelation and phase separation of hyroxypropyl methylcellulose aqueous systems", Polymer, 2002, pp. 5623-5628, vol. 43.

Malamataris, et al., "Effect of particle size and sorbed moisture on the compression behavior of some hydroxypropyl methylcellulose (HPMC) polymers", International Journal of Pharmaceutics, 1994, pp. 205-215, vol. 103.

Handbook of Pharmaceutical Additives, Second Edition, Synapse Information Resourse, Inc., 2006, pp. 20 & 154.

Handbook of Pharmaceutical Excipients, Fifth Edition, The American Pharmaceutical Association and Pharmaceutical Press, 2006, pp. 132-135.

Handbook of Pharmaceutical Excipients, Second Edition, The American Pharmaceutical Association and Pharmaceutical Press, 1994, pp. 84-87.

Avicel Product Selection table, 2008, from FMC website—http://www.fmcbiopolymer.com/Pharmaceutical/-Products/Avicelforsoliddoseforms.aspx.

Methocel Premium Products for Pharmaceutical Applications from Dow Chemical Co. website—http://www.dow.com/dowexcipents/products/methocel.htm.

Methocel Cellulose Ethers—Technical handbook, Dow Chemical Co., 2002.

U.S. Appl. No. 13/503,939, filed Apr. 25, 2012.

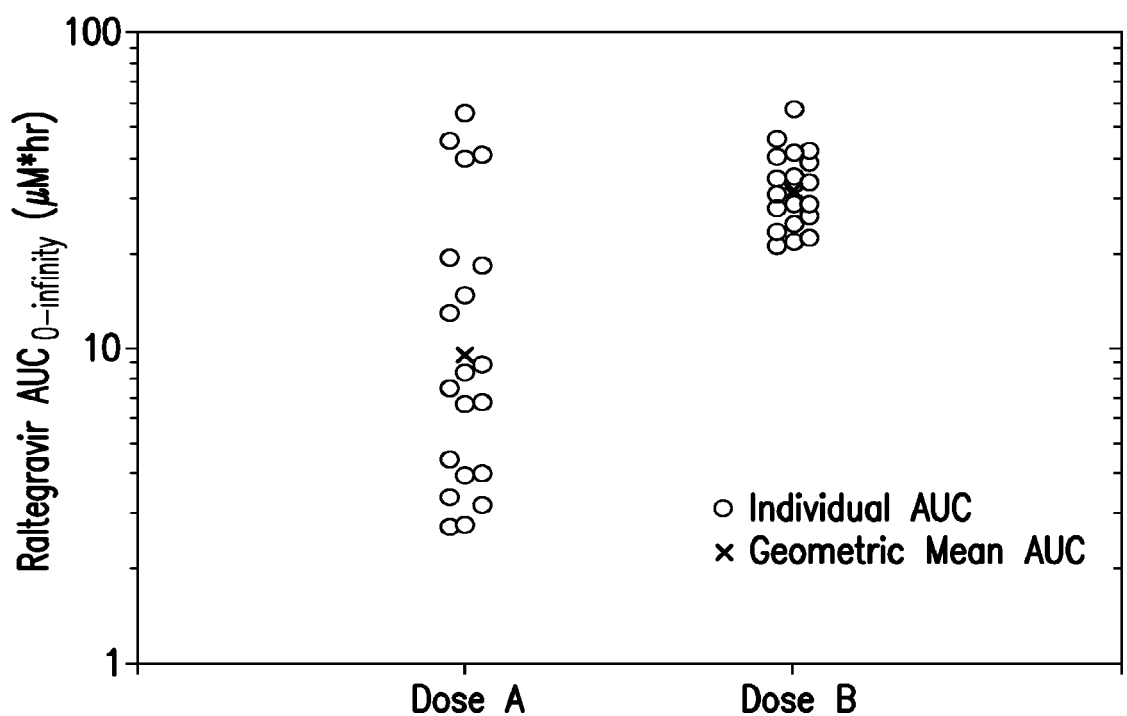

SOLID PHARMACEUTICAL COMPOSITIONS CONTAINING AN INTEGRASE INHIBITOR

CROSS REFERENCE TO RELATED APPLICATIONS

This application is a divisional application of U.S. Ser. No. 13/503,939, filed Apr. 25, 2012, which issued as U.S. Pat. No. 9,649,311, which is a national stage application under 35 U.S.C. 371 of International Patent Application No. PCT/US2010/053507, filed Oct. 21, 2010, which claims priority to U.S. Provisional Application No. 61/254,869, filed Oct. 26, 2009. Each of the aforementioned US, PCT and priority applications is incorporated by reference in its entirety.

FIELD OF THE INVENTION

The present invention is directed to solid pharmaceutical compositions for oral administration, particularly tablets, which comprise raltegravir in the form of a pharmaceutically acceptable salt.

BACKGROUND OF THE INVENTION

The compound N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide (hereinafter referred to as "raltegravir") is a potent HIV integrase inhibitor. The structure of raltegravir is as follows:

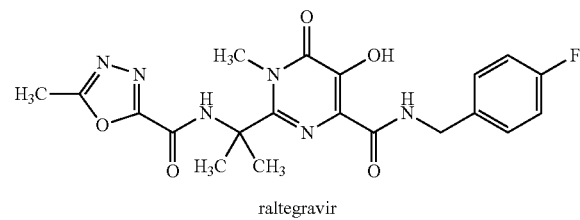 [SMILES: Cc1nnc(C(=O)NC(C)(C)c2nc(C(=O)NCc3ccc(F)cc3)c(O)c(=O)n2C)o1]

raltegravir

Raltegravir, disclosed in U.S. Pat. No. 7,169,780, is the active pharmaceutical ingredient (API) in Isentress® tablets. The tablets contain 400 mg of raltegravir in the form of a potassium salt and are approved by the FDA in combination with other anti-retroviral agents for the treatment of human immunodeficiency virus (HIV-1) infection in adult patients. Isentress® is a first-in-class drug product and an important weapon in the arsenal of drugs available for treating HIV infection. A useful complement to Isentress® would be a raltegravir-containing tablet that is smaller in weight and volume and characterized by providing an improved pharmacokinetic profile.

The following references are of interest as background:

US 2006/0122205 A1 discloses crystalline potassium salts of raltegravir.

US 2007/0292504 A1 discloses pharmaceutical formulations for oral administration in solid dosage forms that contain a base salt of raltegravir and a release rate controlling composition. Example 3 describes the preparation via a dry granulation process of compressed tablets containing raltegravir potassium salt (400 mg free phenol), microcrystalline cellulose, lactose hydrous spray dried, anhydrous dibasic calcium phosphate, HPMC K4M, poloxamer 407, sodium stearyl fumarate, and magnesium stearate.

US 2008/0118559 A1 discloses pharmaceutical formulations for oral administration in solid dosage forms that contain an alkali metal salt of raltegravir and an anti-nucleating agent. Example 3 describes the preparation via a dry granulation process of compressed tablets containing raltegravir potassium salt (100 mg and 25 wt. % on a free phenol basis), microcrystalline cellulose, lactose monohydrate, croscarmellose sodium, HPMC 2910 (6 cp), and magnesium stearate. Example 6 describes the preparation via dry granulation of compressed tablets film-coated with Opadry White and containing raltegravir potassium salt (400 mg and 50 wt. % on a free phenol basis), microcrystalline cellulose, lactose monohydrate, croscarmellose sodium, HPMC 2910 (6 cp), and magnesium stearate.

WO 2009/002823 A2 discloses compressed tablets comprising raltegravir and granules containing atazanavir sulfate and an intragranular lubricant, wherein the granules have an interior section and an exterior surface and at least a portion of the intragranular lubricant is present in the interior section of the granules. The compressed tablets are useful for treating HIV infection.

SUMMARY OF THE INVENTION

The present invention is directed to compressed tablets for oral administration that contain raltegravir as an active pharmaceutical ingredient in the form of a pharmaceutically acceptable salt. More particularly, the present invention includes a compressed tablet which comprises:
(A) an intragranular component comprising:
(i) an effective amount of an alkali metal salt of raltegravir,
(ii) optionally a first superdisintegrant, and
(iii) a binder; and
(B) an extragranular component comprising:
(i) a second superdisintegrant,
(ii) a filler, and
(iii) a lubricant;
with the proviso that the tablet is free of atazanavir or a pharmaceutically acceptable salt thereof.

It is understood that the compressed tablets can include one or more ingredients in addition to those specifically recited in (A) and (B) above, except that the tablet is free of atazanavir or a pharmaceutically acceptable salt of atazanavir. As used herein, the term "free of" a certain substance (e.g., atazanavir or a pharmaceutically acceptable salt thereof) means that the compressed tablet of the invention does not contain the substance. The compressed tablet can include one or more additional ingredients in Component A or in Component B or in each of Components A and B. The compressed tablet can include one or more additional ingredients in one or more additional components. The additional ingredients can be selected from APIs (other than atazanavir and pharmaceutically acceptable salts thereof), excipients, carriers, and the like.

An embodiment of the present invention (alternatively referred to herein as Embodiment E1) is a compressed tablet as just defined above, wherein the first superdisintegrant is present in intragranular component A; i.e., the presence of the first superdisintegrant is not optional. Accordingly, Embodiment E1 is a compressed tablet which comprises:
(A) an intragranular component comprising (i) an effective amount of an alkali metal salt of raltegravir, (ii) a first superdisintegrant, and (iii) a binder; and
(B) an extragranular component comprising (i) a second superdisintegrant, (ii) a filler, and (iii) a lubricant;

with the proviso that the tablet is free of atazanavir or a pharmaceutically acceptable salt thereof.

The compressed tablets of the present invention can provide an improved pharmacokinetic profile compared to poloxamer-containing raltegravir tablets such as those described in US 2007/0292504 which covers Isentress® tablets. More particularly, raltegravir-containing compressed tablets of the present invention have been found to provide a significantly increased drug absorption (i.e., significantly higher AUC) with significantly reduced absorption variability with respect to Isentress® tablets (see Example 3 below). The formulation employed in the tablets of the present invention can permit the preparation of tablets with a larger drug load and a smaller image size than is practical for Isentress® tablets, which thus makes the formulation more attractive for use in fixed-dosed combinations with other APIs.

The present invention also includes methods for preparing the compressed tablets. The present invention further includes use of the compressed tablets for the inhibition of HIV integrase, for the treatment or prophylaxis of HIV infection, or for the treatment, delay in the onset, or prophylaxis of AIDS.

Various embodiments, aspects and features of the present invention are either further described in or will be apparent from the ensuing description, examples and appended claims.

BRIEF DESCRIPTION OF THE DRAWINGS

FIG. 1 is a chart showing the individual and mean AUC values of raltegravir for the dose A and dose B treatment arms of the pharmacokinetic study described in Example 3.

DETAILED DESCRIPTION OF THE INVENTION

The compressed tablets of the present invention comprise an intragranular component and an extragranular component wherein the intragranular component contains an effective amount of raltegravir in the form of a pharmaceutically acceptable salt.

As further described below, the compressed tablets are prepared using a method which involves granulation such that certain of the ingredients are combined prior to the formation of granules and other of the ingredients are added after granulation. The term "intragranular component" refers to the ingredients of the compressed tablet that are incorporated prior to the granulation step, and "extragranular component" refers to the ingredients that are incorporated after granulation.

The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts of raltegravir include base salts; i.e., salts formed by reaction of the drug compound with a base. The raltegravir salt is an alkali metal salt such as a sodium or potassium salt, and is more typically a potassium salt. Alkali metal salts of the compounds can be formed by treating the compound dissolved in a suitable solvent with an aqueous solution of the alkali metal hydroxide (e.g., NaOH or KOH).

The term "effective amount" as used herein means that amount of an API (e.g., raltegravir) that elicits the biological or medicinal response in a tissue, system, animal or human that is being sought by a researcher, veterinarian, medical doctor or other clinician. The effective amount can be a "therapeutically effective amount" for the alleviation of the symptoms of the disease or condition being treated. The effective amount can also be a "prophylactically effective amount" for prophylaxis of the symptoms of the disease or condition being prevented. When the drug compound inhibits the action of an enzyme (e.g., HIV integrase), the term also refers to the amount of active compound sufficient to inhibit the enzyme and thereby elicit the response being sought (i.e., an "inhibition effective amount").

The intragranular component includes, in addition to the raltegravir salt, a binder, and optionally a superdisintegrant. The term "superdisintegrant" refers to a substance, or a mixture of substances, employed in the tablet to facilitate its breakup or disintegration after administration. The intragranular superdisintegrant is suitably croscarmellose sodium, crospovidone, or sodium starch glycolate, and is typically croscarmellose sodium or sodium starch glycolate sodium, and is more typically croscarmellose sodium. The superdisintegrant employed in the intragranular component of the compressed tablet can optionally be a combination of two or more superdisintegrants, such as a combination of croscarmellose sodium and sodium starch glycolate. The superdisintegrants in the combination can be added separately or as a blend for mixing with the other ingredients of the intragranular component.

The term "binder" refers to a substance or mixture of substances that provides or improves the cohesiveness of the granules and can also contribute to the cohesiveness of the compressed tablets. A binder, for example, insures that the tablet remains intact following compression. Suitable binders include such substances as gelatin, guar gum, hydrogenated vegetable oil, and various celluloses. In an aspect of the invention, the binders are low-viscosity binders. The term "low-viscosity" refers to a binder that produces a 2 wt. % (i.e., weight of polymer/weight of water) aqueous solution having a viscosity in a range of from about 2 to about 100 centipoise (cps) at 20° C. (1 cps=1 mPa sec). Low-viscosity binders suitable for use in the compressed tablets of the invention typically produce a 2 wt. % solution having a viscosity in a range of from about 2 to about 50 cps (e.g., from about 3 to about 20 cps) at 20° C. Suitable binders include low-viscosity, water-soluble polymers such as hydroxyalkylcelluloses, alkylcelluloses, and polyvinylpyrrolidones. The low-viscosity binder is typically hydroxypropylmethylcellulose (HPMC), hydroxyethylcellulose (HEC), hydroxypropylcellulose (HPC), polyvinylpyrrolidone (PVP), or methylcellulose. The low-viscosity binder is more typically HPMC, HPC, or PVP. In one aspect of the invention, the low-viscosity binder is an HPMC having a hydroxypropyl content of from about 7 to about 12 wt. %, a methoxy content of from about 28 to about 30 wt. %, and a viscosity for 2% w/w aqueous solutions of from about 3 to about 20 cps. In another aspect, the binder is an HPMC which is U.S. Pharmacopeia standard substitution type 2208, 2906 or 2910, such as HPMC 2910 (6 cps) which is available as PHARMACOAT from Shin-Etsu Chemical Co.

The binder can be a combination of two or more binders. For example, the binder can be a combination of low-viscosity, water-soluble polymers (e.g., two or more HPMC polymers), wherein the polymer mixture produces a 2 wt. % solution with an average viscosity in the low-viscosity range. The average viscosity of the polymer mixture typically differs from the viscosity of each component polymer. The binders in the combination can be added separately or as a mixture for blending with the other ingredients in the intragranular component.

The extragranular component includes a superdisintegrant, a filler and a lubricant. The extragranular superdisintegrant (alternatively referred to herein as the "second superdisintegrant") can be the same or different as the intragranular superdisintegrant (alternatively referred to herein as the "first superdisintegrant"). The extragranular superdisintegrant is suitably croscarmellose sodium, crospovidone, or sodium starch glycolate, and is typically croscarmellose sodium or sodium starch glycolate, and is more typically croscarmellose sodium. In one aspect of the invention, the intragranular component of the compressed tablet does not contain a superdisintegrant and the extragranular component includes a superdisintegrant such as croscarmellose sodium. The compressed tablet preferably contains both an intragranular and an extragranular superdisintegrant. Compressed tablets containing both intragranular and extragranular superdisintegrants are believed to be more robust; i.e., the tablets have better reproducibility in terms of their compaction and dissolution characteristics than analogous tablets containing only extragranular superdisintegrant. Thus, in an aspect of the invention, the tablet contains both an intragranular and an extragranular superdisintegrant and both superdisintegrants are croscarmellose sodium or both are a combination of croscarmellose sodium and sodium starch glycolate. In another aspect, the tablet contains an intragranular and an extragranular superdisintegrants and both are croscarmellose sodium.

A filler (also referred to in the art as a "diluent") is a substance used to impart bulk to the tablet. Suitable fillers include anhydrous dibasic calcium phosphate, dibasic calcium phosphate dihydrate, tribasic calcium phosphate, calcium sulfate, carboxymethylcellulose calcium, microcrystalline cellulose, powdered cellulose, glucose, fructose, lactose, mannitol, dextrin, dextrose, dextrates, kaolin, lactitol, magnesium carbonate, magnesium oxide, maltitol, maltodextrin, maltose, starch, sucrose, trehalose, talc and combinations thereof. In one aspect of the invention, the filler is lactose, microcrystalline cellulose, mannitol, anhydrous dibasic calcium phosphate or dibasic calcium phosphate dihydrate. In another aspect of the invention, the filler is not a reducing sugar; i.e., in this aspect the binder is not glucose, fructose, lactose, maltose, dextrose, or the like. In a feature of this aspect, the filler is microcrystalline cellulose, mannitol, anhydrous dibasic calcium phosphate, dibasic calcium phosphate dihydrate, or a combination thereof. In another feature of this aspect, the filler is microcrystalline cellulose, anhydrous dibasic calcium phosphate, dibasic calcium phosphate dihydrate, or a combination thereof.

In yet another aspect of the invention, the filler is microcrystalline cellulose. An example of a suitable microcrystalline cellulose is one that can be characterized as having a nominal particle size of about 100 μm, a moisture content of from about 3% to about 5%, and a loose bulk density of from about 0.28 to about 0.33 g/cc. A microcrystalline cellulose having the foregoing characteristics is, for example, AVICEL PH-102. Other suitable microcrystalline celluloses are those with the following characteristics:

| Nominal Particle Size μm | Moisture Content (%) | Loose Bulk Density (g/cc) | Example |
|---|---|---|---|
| 50 | 3.0 to 5.0 | 0.26-0.31 | AVICEL PH-101 |
| 50 | ≤3 | 0.26-0.31 | AVICEL PH-103 |
| 20 | ≤5.0 | 0.20-0.30 | AVICEL PH-105 |

Accordingly, suitable forms of microcrystalline cellulose for use in the compressed tablets of the invention include, but are not limited to, the materials sold as AVICEL PH-101, AVICEL PH-102, AVICEL PH-103, and AVICEL PH-105 (all of which are available from FMC Corporation), and combinations thereof. Thus, for example, the microcrystalline cellulose employed in the tablet can be AVICEL PH-102 or AVICEL PH-105 or a combination thereof.

In still another aspect of the invention, the filler is a combination of microcrystalline cellulose and anhydrous dibasic calcium phosphate. An example of a suitable combination is a powder containing about 75% microcrystalline cellulose and about 25% anhydrous dibasic calcium phosphate, wherein the powder is prepared by the wet dispersion and spray drying of the cellulose and the phosphate. Such a product is commercially available as AVICEL DG from FMC Corporation.

The role of the lubricant is to improve the flow of granules resulting from the granulation step prior to their compression and/or to prevent adhesion of the compressed tablet to the compression equipment. Suitable lubricants include calcium stearate, glyceryl monostearate, glyceryl palmitostearate, hydrogenated castor oil, hydrogenated vegetable oil, light mineral oil, magnesium stearate, mineral oil, polyethylene glycol, stearic acid, talc, zinc stearate, and sodium stearyl fumarate. In an aspect of the invention, the lubricant is magnesium stearate, stearic acid, sodium stearyl fumarate, or a combination of two or more thereof. In another aspect, the lubricant is magnesium stearate. When a combination of lubricants is employed, the lubricants can be added separately or as a mixture to the granules.

The compressed tablet of the invention does not contain atazanavir or a pharmaceutically acceptable salt thereof such as atazanavir sulfate. Atazanavir sulfate has the structure:

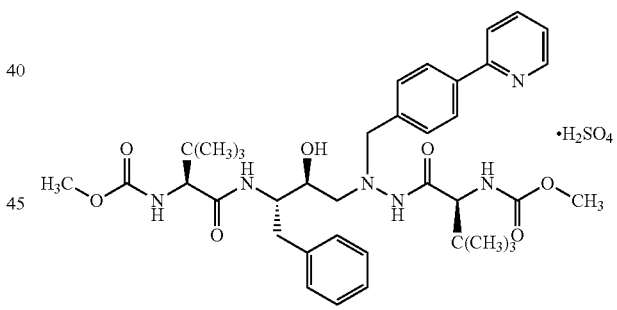

Further description of atazanavir, atazanavir sulfate, and methods for preparation and use can be found, for example, in U.S. Pat. No. 6,087,383, US 2005/0256202 A1 and WO 2009/002823 A2. Atazanavir is commercially available as a prescription medicine from Bristol-Myers Squibb Company under the tradename Reyataz® (atazanavir sulfate) in the form of 100, 150, 200 and 300 mg capsules.

Unless clear from the context or expressly stated otherwise herein, the weight percent of raltegravir in the compressed tablet is expressed in terms of the free phenol even though it is employed in the form of a salt. The weight percents of the tablet ingredients (e.g., the first and second superdisintegrants, the binder, the filler, the lubricant, etc.) are based upon the total weight of the tablet.

A second embodiment of the present invention (Embodiment E2) is a compressed tablet as originally defined above (i.e., as defined in the Summary of the Invention) wherein:

(A)(i) the alkali metal salt of raltegravir is employed on a free phenol basis in an amount of at least about 30 wt. %;

(A)(ii) the first superdisintegrant is employed in an amount in a range of from zero to about 12 wt. %;

(A)(iii) the binder is employed in an amount in a range of from about 0.5 wt. % to about 7 wt. %;

(B)(i) the second superdisintegrant is employed in an amount in a range of from about 3 wt. % to about 20 wt. %;

(B)(ii) the filler is employed in an amount in a range of from about 10 wt. % to about 40 wt. %; and (B)(iii) the lubricant is employed in an amount in a range of from about 0.5 wt. % to about 2.5 wt. %;

wherein the total amount of superdisintegrant is in a range of from about 6 wt. % to about 20 wt. %; and wherein the weight percent of each ingredient in the compressed tablet is based on the total weight of the compressed tablet.

A third embodiment of the present invention (Embodiment E3) is a compressed tablet as defined in Embodiment E1, wherein:

(A)(i) the alkali metal salt of raltegravir is employed on a free phenol basis in an amount of at least about 30 wt. %;

(A)(ii) the first superdisintegrant is employed in an amount in a range of from about 3 wt. % to about 12 wt. %;

(A)(iii) the binder (e.g., a low-viscosity binder) is employed in an amount in a range of from about 0.5 wt. % to about 7 wt. %;

(B)(i) the second superdisintegrant is employed in an amount in a range of from about 3 wt. % to about 15 wt. %;

(B)(ii) the filler is employed in an amount in a range of from about 10 wt. % to about 40 wt. %; and (B)(iii) the lubricant is employed in an amount in a range of from about 0.5 wt. % to about 2.5 wt. %;

wherein the total amount of superdisintegrant is in a range of from about 6 wt. % to about 20 wt. %; and wherein the weight percent of each ingredient in the compressed tablet is based on the total weight of the compressed tablet.

A fourth embodiment of the present invention (Embodiment E4) is a compressed tablet as originally defined above or as defined in any of Embodiments E1 to E3, wherein:

(A)(ii) the first superdisintegrant is selected from the group consisting of croscarmellose sodium, sodium starch glycolate, crospovidone, and combinations thereof;

(A)(iii) the binder has a viscosity in a range of from about 2 to about 100 centipoise (cp) at 20° C. and is selected from the group consisting of HPMC, HPC, PVP and combinations thereof;

(B)(i) the second superdisintegrant is selected from the group consisting of croscarmellose sodium, sodium starch glycolate, crospovidone, and combinations thereof;

(B)(ii) the filler is selected from the group consisting of microcrystalline cellulose, mannitol, lactose, Ca phosphate, and combinations thereof; and (B)(iii) the lubricant is selected from the group consisting of Mg stearate, stearic acid, sodium stearyl fumarate, and combinations thereof.

In a first aspect of Embodiment E4:

(A)(ii) the first superdisintegrant is selected from the group consisting of croscarmellose sodium, sodium starch glycolate, and crospovidone;

(A)(iii) the binder has a viscosity in a range of from about 2 to about 100 centipoise (cp) at 20° C. and is selected from the group consisting of HPMC, HPC, and PVP;

(B)(i) the second superdisintegrant is selected from the group consisting of croscarmellose sodium, sodium starch glycolate, and crospovidone;

(B)(ii) the filler is selected from the group consisting of microcrystalline cellulose, mannitol, lactose, Ca phosphate, and combinations thereof; and (B)(iii) the lubricant is selected from the group consisting of Mg stearate, stearic acid, sodium stearyl fumarate, and combinations thereof. In a feature of the first aspect, the filler is selected from the group consisting of microcrystalline cellulose, Ca phosphate, and combinations thereof. In another feature of the first aspect of Embodiment E4, the filler is microcrystalline cellulose. In still another feature of the first aspect of Embodiment E4, the filler is a combination of microcrystalline cellulose and dibasic Ca phosphate (e.g., anhydrous dibasic Ca phosphate).

In a second aspect of Embodiment E4, the filler is selected from the group consisting of microcrystalline cellulose, Ca phosphate, and combinations thereof. In a third aspect of Embodiment E4, the filler is microcrystalline cellulose. In a fourth aspect of Embodiment E4, the filler is a combination of microcrystalline cellulose and dibasic Ca phosphate (e.g., anhydrous dibasic Ca phosphate).

Another embodiment of the present invention (Embodiment E5) is a compressed tablet as originally defined above or as defined in any of the foregoing embodiments, wherein:

(A)(i) the alkali metal salt of raltegravir is a Na or K salt employed in an amount in a range of from about 50 wt. % to about 65 wt. %;

(A)(ii) the first superdisintegrant is employed in an amount in a range of from about 5 wt. % to about 10 wt. %;

(A)(iii) the binder is employed in an amount in a range of from about 2 wt. % to about 6 wt. %;

(B)(i) the second superdisintegrant is employed in an amount in a range of from about 6 wt. % to about 12 wt. %;

(B)(ii) the filler is employed in an amount in a range of from about 6 wt. % to about 25 wt. %; and (B)(iii) the lubricant is employed in an amount in a range of from about 1 wt. % to about 2.5 wt. %;

wherein the total amount of superdisintegrant is in a range of from about 10 wt. % to about 18 wt. %.

Another embodiment of the present invention (Embodiment E6) is identical to Embodiment E5, except that the filler—(B)(ii)—is employed in an amount in a range of from about 10 wt. % to about 25 wt. %.

In an aspect of Embodiment E5 and Embodiment E6, the first superdisintegrant and the second superdisintegrant are the same substance or the same combination of substances.

Another embodiment of the present invention (Embodiment E7) is a compressed tablet as originally defined above or as defined in any one of Embodiments E1 to E6, wherein:

(A)(ii) the first superdisintegrant is intragranular croscarmellose Na;

(A)(iii) the binder is HPMC;

(B)(i) the second superdisintegrant is extragranular croscarmellose Na;

(B)(ii) the filler is microcrystalline cellulose or a combination of microcrystalline cellulose and dibasic Ca phosphate (e.g., anhydrous dibasic Ca phosphate); and (B)(iii) the lubricant is Mg stearate.

Another embodiment of the present invention (Embodiment E8) is identical to Embodiment E7, except that the filler is microcrystalline cellulose (i.e., the filler is not a combination of microcrystalline cellulose and dibasic Ca phosphate).

Another embodiment of the present invention (Embodiment E9) is a compressed tablet as defined in Embodiment E8, wherein:

(A)(i) the alkali metal salt of raltegravir is a Na or K salt employed in an amount in a range of from about 55 wt. % to about 60 wt. %;

(A)(ii) the intragranular croscarmellose Na is employed in an amount in a range of from about 5 wt. % to about 7 wt. %;

(A)(iii) the HPMC is employed in an amount in a range of from about 3 wt. % to about 5 wt. %;

(B)(i) the extragranular croscarmellose Na is employed in an amount in a range of from about 8 wt. % to about 10 wt. %;

(B)(ii) the microcrystalline cellulose is employed in an amount in a range of from about 16 wt. % to about 18 wt. %; and (B)(iii) the magnesium stearate is employed in an amount in a range of from about 1 wt. % to about 2 wt. %;

wherein the total amount of croscarmellose sodium is in a range of from about 13 wt. % to about 17 wt. %.

Another embodiment of the present invention (Embodiment E10) is a compressed tablet as defined in Embodiment E7, wherein:

(A)(i) the sodium or potassium salt of raltegravir is employed in an amount in a range of from about 55 wt. % to about 65 wt. % on a free phenol basis;

(A)(ii) the intragranular croscarmellose Na is employed in an amount in a range of from about 5 wt. % to about 8 wt. %;

(A)(iii) the HPMC is employed in an amount in a range of from about 3 wt. % to about 5 wt. %;

(B)(i) the extragranular croscarmellose Na is employed in an amount in a range of from about 8 wt. % to about 10 wt. %;

(B)(ii) the filler is a combination of microcrystalline cellulose and dibasic Ca phosphate is employed in an amount in a range of from about 7 wt. % to about 10 wt. %; and (B)(iii) the magnesium stearate is employed in an amount in a range of from about 1 wt. % to about 2 wt. %;

wherein the total amount of croscarmellose sodium is in a range of from about 13 wt. % to about 17 wt. %.

Another embodiment of the present invention (Embodiment E11) is a compressed tablet as originally defined above or as defined in any one of Embodiments E1 to E10, wherein the alkali metal salt of raltegravir is employed on a free phenol basis in an amount in a range of from about 200 mg to about 600 mg per unit dose.

Another embodiment of the present invention (Embodiment E12) is a compressed tablet as originally defined above or as defined in any one of Embodiments E1 to E11, wherein alkali metal salt of raltegravir is a potassium salt of raltegravir.

Another embodiment of the present invention (Embodiment E13) is a compressed tablet as defined in Embodiment E7, wherein the tablet has the following composition:

| Ingredient | Relative Amount (wt. %) |
|---|---|
| raltegravir K salt | 62.1 |
| | (57.1 on free phenol basis) |
| croscarmellose Na (intragranular) | 6.2 |
| HPMC2910 (6 cp) | 4.1 |
| microcrystalline cellulose, having a nominal particle size of 100 μm, moisture content of 3.0 to 5.0%, and loose bulk density = 0.26 to 0.31 g/cc [1] | 17.1 |
| croscarmellose Na (extragranular) | 9.0 |
| Mg stearate | 1.5 |
| Total | 100 |

[1] A suitable microcrystalline cellulose is AVICEL PH-102.

In an aspect of this embodiment, the unit dosage amount of raltegravir potassium in the tablet is 434.4 mg (400 mg in terms of the free phenol).

Another embodiment of the present invention (Embodiment E14) is a compressed tablet as defined in Embodiment E7, wherein the tablet has the following composition:

| Ingredient | Relative Amount (wt. %) |
|---|---|
| raltegravir K salt | 70.0 |
| | (64.5 on free phenol basis) |
| croscarmellose Na (intragranular) | 7.0 |
| HPMC2910 (6 cp) | 4.7 |
| combination of microcrystalline cellulose & dibasic Ca phosphate which is about 75% microcrystalline cellulose and about 25% anhydrous dibasic Ca phosphate in the form of a powder prepared by the wet dispersion and spray drying of the cellulose and the phosphate[1] | 7.8 |
| croscarmellose Na (extragranular) | 9.0 |
| Mg stearate | 1.5 |
| Total | 100 |

[1] A suitable filler is AVICEL DG.

In an aspect of this embodiment, the unit dosage amount of raltegravir potassium in the tablet is 434.4 mg (400 mg in terms of the free phenol).

Another embodiment of the present invention (Embodiment E15) is a compressed tablet as originally defined above or as defined in any one of Embodiments E1 to E14, wherein alkali metal salt of raltegravir is a potassium salt of raltegravir, which is the Form 1 crystalline potassium salt of raltegravir. The Form 1 crystalline salt is the crystalline salt described and characterized in Example 2 in US 2006/0122205 A1. The Form 1 salt of raltegravir is characterized by an X-ray powder diffraction pattern obtained using copper $K_\alpha$ radiation (i.e., the radiation source is a combination of Cu $K_{\alpha 1}$ and $K_{\alpha 2}$ radiation) which comprises 2Θ values (i.e., reflections at 2Θ values) in degrees of 5.9, 20.0 and 20.6. In an aspect of this embodiment, the Form 1 crystalline potassium salt of raltegravir is characterized by an X-ray powder diffraction pattern obtained using copper $K_\alpha$ radiation which comprises 2Θ values in degrees of 5.9, 12.5, 20.0, 20.6 and 25.6. A representative XRPD pattern for Form 1 is presented in FIG. 1 of US 2006/0122205 A1.

Another embodiment of the present invention (Embodiment E16) is a compressed tablet as originally defined above or as defined in any one of Embodiments E1 to E15, wherein the tablet is free of reducing sugars; i.e., a reducing sugar is not contained in the tablet. Reducing sugars are sugars which act as reducing agents and readily reduce alkaline solutions of copper salts. A sugar which produces a brick red color when tested with Benedict's reagent or Fehling's solution is a reducing sugar. The color in the test solution is due to the reduction of Cu(II) ions to copper(I) oxide by the sugar. Reducing sugars include glucose, fructose, lactose, arabinose and maltose.

Compositions containing a reducing sugar and an amine are susceptible to the Maillard condensation reaction which can lead to the formation of brown-colored degradation products. Tablets of the invention that are free of reducing sugars are therefore more compatible with amine-containing substances that may be present in the tablet. The use of tablets free of reducing sugars is particularly attractive when the tablet includes a second active pharmaceutical ingredient having one or more amine groups (e.g., a monolithic tablet containing a fixed-dose combination of raltegravir and an amine-containing HIV antiviral).

Another embodiment of the present invention (Embodiment E17) is a compressed tablet as originally defined above or as defined in any one of Embodiments E1 to E15, wherein the tablet is free of poloxamer; i.e., a poloxamer is not contained in the tablet. Poloxamers are block copolymers of ethylene oxide and propylene oxide. The copolymers typically have an average molecular weight in a range of from about 1000 to about 20,000 and an oxyethylene content of from about 40 to about 90 wt. % Poloxamers can be used in pharmaceutical formulations as, for example, solubilizing agents, emulsifying agents, or wetting agents. Representative poloxamers include poloxamer 188, poloxamer 237, poloxamer 338, and poloxamer 407. In certain tablet formulations, a high level of poloxamer can adversely affect compaction and can result in tablet material sticking to the die wall during compressive formation of the tablet. A high poloxamer level can also inhibit the absorption of certain active ingredients. Isentress® contains a relatively high level of poloxamer and the tablets are characterized by having a relatively slow release of raltegravir following administration. It is believed that the introduction of another HIV antiviral to such a formulation to provide a fixed-dose combination with raltegravir could adversely affect the absorption of the antiviral.

Another embodiment of the present invention (Embodiment E18) is a compressed tablet as originally defined above or as defined in any one of Embodiments E1 to E15, wherein the tablet is free of poloxamers and reducing sugars; i.e., neither a poloxamer nor a reducing sugar is contained in the tablet.

Another embodiment of the present invention (Embodiment E19) is a compressed tablet as originally defined above or as defined in any one of Embodiments E1 to E18, wherein the disintegration time of the compressed tablet is less than about 15 minutes. In an aspect of this embodiment, the disintegration time is in a range of from about 5 minutes to about 12 minutes. The disintegration time is determined in the manner described in Example 2.

The compressed tablets as originally described above and as described in each of the foregoing aspects and embodiments can be prepared via wet granulation in which the overall particle size of a suitable formulation is increased through the permanent aggregation of smaller particles. Wet granulation involves wetting a well-mixed blend of the dry intragranular ingredients (e.g., the raltegravir salt, the first superdisintegrant, and the binder) with sufficient solvent (e.g., water or water with an alcohol co-solvent) to moisten the dry blend such that particles in the blend tack to one another to form larger particles, and then sieving, comminuting, or otherwise manipulating the size of the particles. Once formed, the resulting wet granulate can then be dried and milled into suitably sized particles (i.e., granules), the granules blended with a lubricant and optionally other extragranular ingredients (e.g., the second superdisintegrant and the filler), and the lubricated granules compressed into tablets.

The compressed tablets can be sugar coated to mask any unpleasant taste or film coated (e.g., polymer coated) to protect the tablet from atmospheric degradation. The coating must also not adversely affect release of the drug following oral administration. A suitable film coating suspension is Opadry II (39K) (available from Colorcon, West Point, Pa.), which is a hydroxypropyl methylcellulose (HPMC)-based polymer, with triacetin, lactose, and titanium dioxide. The films can be applied by spraying the suspension on the tablets and then drying. Suitable film coating techniques are described in *Remington's Pharmaceutical Sciences, 18$^{th}$ edition*, edited by A. R. Gennaro, 1990, Mack Publishing Co., pp. 1665-1675, and in *Remington—The Science and Practice of Pharmacy,* 21st edition, 2005, Chapter 46.

Technology and equipment suitable for preparing compressed tablets of the present invention are described in *Remington's Pharmaceutical Sciences, 18$^{th}$ edition*, edited by A. R. Gennaro, 1990, Chapter 89 and in *Remington—The Science and Practice of Pharmacy,* 21st edition, 2005, Chapter 45.

The present invention includes a process (alternatively referred to herein as "Process P1" or the "P1 process") for preparing a compressed tablet comprising an effective amount of an alkali metal salt of raltegravir, optionally a first superdisintegrant, a binder (e.g., a low-viscosity binder), a second superdisintegrant, a filler, and a lubricant; wherein the method comprises:

(A) dry mixing the raltegravir salt, the first superdisintegrant (optional) and the binder to obtain a dry blend;

(B) wet granulating the dry blend and then optionally milling or sieving the wet granulated mixture;

(C) drying the wet granulated mixture of Step B to obtain dried granules;

(D) milling and sieving the dried granules of Step C;

(E) mixing the milled, sieved granules resulting from Step D with the second superdisintegrant, the filler and the lubricant to obtain a lubricated granular blend; and (F) compressing the lubricated granular blend of Step E to obtain the tablet; with the proviso that the process does not employ and the resulting tablet does not contain atazanavir or a pharmaceutically acceptable salt thereof.

The mixing is conducted in Step A for a time sufficient to obtain a relatively uniform blend of the ingredients. The mixing can be performed in any suitable mixing equipment such as a high shear granulator, a V-blender, or a bin-blender. The wet granulation of Step B can be conducted by adding the granulating fluid (typically water) to the mixer containing the blended ingredients and mixing the wet ingredients. The wet granulate can then be milled or sieved in a separate operation (e.g., by forcing the wet granulate through a mesh screen of suitable size). Alternatively, some mixers are equipped with a chopper blade that operates independently of the mixing blades, obviating the need for a separate milling/sieving operation. The drying in Step C can be conducted in any convenient way, such as via tray drying or fluid bed drying at a temperature in a range of about 40° C. to about 90° C. The granulate is typically dried to an LOD of about 0.5-3%. The milling and sieving of Step D is conducted to achieve a suitable particle size; e.g., particles with an average diameter in a range of from about 50 to 1200 microns. The mixing in Step E is conducted for a time sufficient to obtain a uniform blend of the granules with the extragranular ingredients. In an aspect of Process P1, Step E comprises (e-i) mixing the milled, sieved granules resulting from Step D with the second superdisintegrant and the filler and then (e-ii) adding the lubricant to the blend resulting from sub-step e(i) to obtain a lubricated granular blend. The granular blend is then compressed into a tablet in Step F using a standard tablet press such as a rotary press to provide tablets with, e.g., a circular or oval shape. Unless expressly stated otherwise (as in Step C), the steps of Process P1 are conducted under ambient conditions; i.e., at or near about 25° C.

Granular blends prepared in accordance with Process P1 can have beneficial flow and compression properties. For example, granular blends containing the K salt of raltegravir prepared as described in Example 1 below have excellent flow properties and a reduced tendency to stick or adhere to compression tooling in comparison to analogous dry granulation blends described in US 2007/0292504 A1 (see Example 3 in US '504 and Reference Example 1 hereinbelow) and in US 2008/0118559 A1 (see Example 6 in US '559).

Embodiments of the P1 process include the process as just described incorporating one or more of the features (i) to (xiv) as follows:

(i-a) the alkali metal salt of raltegravir is a sodium salt or a potassium salt of Compound I;

(i-b) the alkali metal salt of raltegravir is a potassium salt of raltegravir; or (i-c) the alkali metal salt of raltegravir is the Form 1 crystalline potassium salt of raltegravir;

(ii-a) the alkali metal salt of raltegravir is employed in an amount of at least about 30 wt. % on a free phenol basis;

(ii-b) the alkali metal salt of raltegravir is a Na or K salt employed in an amount in a range of from about 50 wt. % to about 65 wt. % on a free phenol basis;

(ii-c) the alkali metal salt of raltegravir (e.g., a K salt of raltegravir) is employed in an amount in a range of from about 55 wt. % to about 60 wt. % on a free phenol basis; or (ii-d) the alkali metal salt of raltegravir (e.g., a K salt of raltegravir) is employed in an amount in a range of from about 55 wt. % to about 65 wt. % on a free phenol basis;

(iii-a) the first superdisintegrant is selected from the group consisting of croscarmellose sodium, sodium starch glycolate, crospovidone, and combinations thereof;

(iii-b) the first superdisintegrant is selected from the group consisting of croscarmellose sodium, sodium starch glycolate, and crospovidone; or (iii-c) the first superdisintegrant is croscarmellose sodium;

(iv-a) the first superdisintegrant is employed in an amount in a range of from zero wt. % to about 12 wt. %;

(iv-b) the first superdisintegrant is employed in an amount in a range of from about 3 wt. % to about 12 wt. %;

(iv-c) the first superdisintegrant is employed in an amount in a range of from about 5 wt. % to about 10 wt. %; or (iv-d) the first superdisintegrant (e.g., croscarmellose Na) is employed in an amount in a range of from about 5 wt. % to about 7 wt. %;

(v-a) the binder has a viscosity in a range of from about 2 to about 100 centipoise (cp) at 20° C. and is selected from the group consisting of HPMC, HPC and PVP; or (v-b) the binder is HPMC;

(vi-a) the binder is employed in an amount in a range of from about 0.5 wt. % to about 7 wt. %; or (vi-b) the binder is employed in an amount in a range of from about 2 wt. % to about 6 wt. %; or (vi-c) the binder (e.g., HPMC) is employed in an amount in a range of from about 3 wt. % to about 5 wt. %;

(vii-a) the second superdisintegrant is optionally the same as the first superdisintegrant and is selected from the group consisting of croscarmellose sodium, sodium starch glycolate, crospovidone and combinations thereof;

(vii-b) the second superdisintegrant is optionally the same as the first superdisintegrant and is selected from the group consisting of croscarmellose sodium, sodium starch glycolate, and crospovidone; or (vii-c) the second superdisintegrant is optionally the same as the first superdisintegrant and is croscarmellose sodium;

(viii-a) the second superdisintegrant is employed in an amount in a range of from about 3 wt. % to about 20 wt. %; (in a sub-feature of viii-a, the first superdisintegrant is employed in the amount set forth in feature iv-a, the second superdisintegrant is employed as set forth in this feature, and the total amount of superdisintegrant is in a range of from about 6 wt. % to about 20 wt. %)

(viii-b) the second superdisintegrant is employed in an amount in a range of from about 3 wt. % to about 15 wt. %; (in a sub-feature of viii-b, the first superdisintegrant is employed in the amount set forth in feature iv-b, the second superdisintegrant is employed as set forth in this feature, and the total amount of superdisintegrant is in a range of from about 6 wt. % to about 20 wt. %)

(viii-c) the second superdisintegrant is employed in an amount in a range of from about 6 wt. % to about 12 wt. %; (in a sub-feature of viii-c, the first superdisintegrant is employed in the amount set forth in feature iv-c, the second superdisintegrant is employed as set forth in this feature, and the total amount of superdisintegrant is in a range of from about 10 wt. % to about 18 wt. %) or (viii-d) the second superdisintegrant (e.g., croscarmellose Na) is employed in an amount in a range of from about 8 wt. % to about 10 wt. %; (in a sub-feature of viii-d, the first superdisintegrant is employed in the amount set forth in feature iv-d, the second superdisintegrant is employed as set forth in this feature, and the total amount of superdisintegrant is in a range of from about 13 wt. % to about 17 wt. %)

(ix-a) the filler is selected from the group consisting of microcrystalline cellulose, mannitol, lactose, Ca phosphate, and combinations thereof, (ix-b) the filler is microcrystalline cellulose (e.g., AVICEL PH-102 or the like); or (ix-c) the filler is a combination of microcrystalline cellulose and dibasic Ca phosphate (e.g., AVICEL DG or the like);

(x-a) the filler is employed in an amount in a range of from about 10 wt. % to about 40 wt. %; or (x-b) the filler is employed in an amount in a range of from about 10 wt. % to about 25 wt. %;

(x-c) the filler (e.g., microcrystalline cellulose) is employed in an amount in a range of from about 16 wt. % to about 18 wt. %; or (x-d) the filler (e.g., a combination of microcrystalline cellulose and dibasic Ca phosphate) is employed in an amount in a range of from about 7 wt. % to about 10 wt. %;

(xi-a) the lubricant is selected from the group consisting of Mg stearate, stearic acid, sodium stearyl fumarate, and combinations thereof, or (xi-b) the lubricant comprises magnesium stearate;

(xii-a) the lubricant is employed in an amount in a range of from about 0.5 wt. % to about 2.5 wt. %; or (xii-b) the lubricant is employed in an amount in a range of from about 1 wt. % to about 2.5 wt. %; or (xii-c) the lubricant (e.g., magnesium stearate) is employed in an amount in a range of from about 1 wt. % to about 2 wt. %;

(xiii-a) the process further comprises: (F) coating the compressed tablet; or (xiii-b) the process further comprises: (F) coating the compressed tablet with a film coating suspension (e.g., Opadry II HP) to afford a coated tablet in which the coating is from about 2 to about 4% of the weight of the compressed tablet; and (xiv-a) the alkali metal salt of raltegravir (e.g., potassium salt of raltegravir) is employed in a per tablet amount in a range of from about 200 mg to about 600 mg on a free phenol basis; or (xiv-b) the alkali metal salt of raltegravir (e.g., potassium salt of raltegravir) is employed in a per tablet amount of about 200 mg, 300 mg, 400 mg, 500 mg, or 600 mg on a free phenol basis.

It is understood that each incorporation of a single one of the foregoing features (i) to (xiv) into Process P1 as originally described constitutes an embodiment of Process P1. It is also understood that each incorporation of two or more of the features (i) to (xiv) into Process P1 as originally described constitutes an embodiment of Process P1. Any combination of features (i) to (xiv) is within the scope of Process P1, unless such combination is internally inconsistent or otherwise would result in an inoperative process.

Another embodiment of Process P1 is Process P1 as originally described above, wherein the identity and amount of each of the ingredients employed in the process is as set forth for the compressed tablet described above in Embodiment E13.

Another embodiment of Process P1 is Process P1 as originally described above, wherein the identity and amount of each of the ingredients employed in the process is as set forth for the compressed tablet described above in Embodiment E14.

The present invention also includes a compressed tablet prepared by the Process P1 as originally set forth above or as set forth in any of the foregoing embodiments of the P1 process.

The compressed tablets of the present invention are useful in the inhibition of HIV integrase, the treatment or prophylaxis of infection by HIV and the treatment, prophylaxis, or the delay in the onset of consequent pathological conditions such as AIDS. Treating AIDS, the prophylaxis of AIDS, delaying the onset of AIDS, treating HIV infection, or prophylaxis of HIV infection is defined as including, but not limited to, treatment or prophylaxis of a wide range of states of HIV infection: AIDS, ARC, both symptomatic and asymptomatic, and actual or potential exposure to HIV. For example, the tablets of this invention are useful in the treatment or prophylaxis of infection by HIV after suspected past exposure to HIV by such means as blood transfusion, exchange of body fluids, bites, accidental needle stick, or exposure to patient blood during surgery.

The present invention includes a method for inhibiting HIV integrase (e.g., HIV-1 integrase) in a subject in need thereof which comprises administering to the subject the compressed tablet as originally defined above in the Summary of the Invention. The invention also includes a method for the treatment or prophylaxis of HIV infection (e.g., HIV-1 infection) or for the treatment, prophylaxis, or delay in the onset of AIDS (e.g., AIDS caused by HIV-1) in a subject in need thereof, which comprises administering to the subject the compressed tablet of the invention as originally defined above. In these methods, the compressed tablet of the present invention can optionally be employed in combination with one or more anti-HIV agents selected from HIV antiviral agents, anti-infective agents, and immunomodulators. Embodiments of these methods include the methods as just described wherein the compressed tablet is a tablet as set forth in any one of the foregoing embodiments thereof (e.g., the tablets as described Embodiments E1 to E19 and the compressed tablets resulting from the P1 process).

The term "subject" (used interchangeably herein with "patient") refers to an animal, preferably a mammal, most preferably a human, who has been the object of treatment, observation or experiment.

When a tablet of the present invention is employed or administered in combination with another agent (e.g., an anti-HIV agent), the tablet and the agent can be administered separately or together, and when administered separately, the tablet and agent can be given concurrently or at different times (e.g., alternately).

The present invention also includes a compressed tablet for oral administration which is the compressed tablet as originally defined and described in the Summary of the Invention (i) for use in, (ii) for use as a medicament for, or (iii) for use in the preparation or manufacture of a medicament for: (a) therapy (e.g., of the human body), (b) medicine, (c) inhibition of HIV integrase, (d) treatment or prophylaxis of infection by HIV, or (e) treatment, prophylaxis of, or delay in the onset or progression of AIDS. Embodiments of these uses include the uses as just described wherein the compressed tablet of the invention as originally defined is replaced with the above-described embodiments thereof (which include, inter alia, the compressed tablets as set forth in Embodiments E1 to E19 and the compressed tablets resulting from the P1 process). In these uses, the compressed tablets of the present invention can optionally be employed in combination with one or more anti-HIV agents selected from HIV antiviral agents (other than atazanavir and pharmaceutically acceptable salts thereof), anti-infective agents, and immunomodulators.

An "anti-HIV agent" is any agent which is directly or indirectly effective in the inhibition of HIV integrase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compressed tablets of this invention may be effectively administered, whether at periods of pre-exposure and/or post-exposure, in combination with effective amounts of one or more HIV antivirals, imunomodulators, antiinfectives, or vaccines useful for treating HIV infection or AIDS, such as those disclosed in Table 1 of WO 01/38332 or in the Table in WO 02/30930 except for atazanavir and pharmaceutically acceptable salts thereof. Suitable HIV antivirals for use in combination with the compounds of the present invention include, for example, those listed in Table A as follows:

TABLE A

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |

TABLE A-continued

| Name | Type |
| --- | --- |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, nelfinavir mesylate.

It is understood that the scope of combinations of the compressed tablet of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of HIV infection or AIDS, excluding compositions containing atazanavir or a pharmaceutically acceptable salt thereof. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and subsequent editions thereof.

It is further understood that the uses and methods of treatment set forth herein exclude the administration of the compressed tablets and fixed dose combinations (described below) of the invention with atazanavir or a pharmaceutically acceptable salt thereof.

The compressed tablets of the invention can suitably contain from about 50 mg to about 800 mg of raltegravir per tablet, and typically contain from about 100 mg to about 700 mg per tablet, and more typically contain from about 200 mg to about 600 mg per tablet. The specific dose level and frequency of dosage can vary from patient to patient due, for example, to a patent's age, body weight, general health, sex, and diet. The appropriate dose level of raltegravir suitable for a particular patient can be determined by the person of ordinary skill in the art without undue experimentation. It is believed that compressed tablets of the invention containing from 200 to 600 mg of raltegravir administered orally to adult humans once or twice per day can be effective in treating HIV infection.

The present invention also includes a solid fixed-dose combination (alternatively referred to herein as combination "FDC") for oral administration which comprises a first part containing an effective amount of an alkali metal salt of raltegravir, wherein the first part comprises the intragranular component and extragranular component employed in the compressed tablet as originally described in the Summary of the Invention or as described in any one of the aspects or embodiments (e.g., Embodiments E1 to E19) thereof; and a second part which comprises a formulation comprising an effective amount of another anti-HIV agent, provided that the fixed-dose combination is free of atazanavir or a pharmaceutically acceptable salt thereof. The anti-HIV agent in the second part can be any anti-HIV agent as defined and described above, except for atazanavir or a pharmaceutically acceptable salt thereof. In one embodiment (Embodiment FDC-E1) the anti-HIV agent in the second part is an HIV attachment inhibitor, a CCR5 inhibitor, a CXCR4 inhibitor, an HIV cell fusion inhibitor, HIV integrase inhibitor, a HIV nucleoside reverse transcriptase inhibitor, an HIV non-nucleoside reverse transcriptase inhibitor, or an HIV protease inhibitor (other than atazanavir or a pharmaceutically acceptable salt thereof). In another embodiment (Embodiment FDC-E2), the anti-HIV agent in the second part is selected from the group consisting of the agents listed in Table A above.

Another embodiment of the fixed-dose combination (Embodiment FDC-E3) is the combination as originally described or as described in either Embodiment FDC-E1 and FDC-E2, wherein the combination is a bilayer compressed tablet, in which the first part is in one layer and the second part is in a second layer. Bilayer tablets can be prepared by compressing the first part and the second part together. Bilayer tablets can alternatively be prepared by introducing the first or second part in a tablet press; compressing that part to form a first tablet layer; introducing the other of the first and second parts to the tablet press; and compressing both the first and second parts to provide a bilayer tablet.

Another embodiment of the fixed-dose combination (Embodiment FDC-E4) is the combination as originally described or as described in either Embodiment FDC-E1 and FDC-E2, wherein the combination is a monolithic compressed tablet, wherein the first part and the second part are in the same layer. Monolithic tablets can be prepared by mixing the first and second parts together and the compressing the mixture in a tablet press.

Another embodiment of the fixed-dose combination (Embodiment FDC-E5) is the combination as originally described or as described in any of the foregoing embodiments FDC-E1 to FDC-E4, wherein the combination is sugar-coated and/or film-coated in the manner described above.

Abbreviations employed herein include the following: API=active pharmaceutical ingredient; APCI=atmospheric pressure chemical ionization (mass spectroscopy); cp=centipoise; CPCG-3=Glatt Powder-Coater-Granulator-3; EDTA=ethylenediaminetetraacetic acid; EG=extragranular; g=gram(s); HEC=hydroxyethylcellulose; HPC=hydroxypropylcellulose; HPMC=hydroxypropylmethylcellulose; HPLC=high-performance liquid chromatography; IG=intragranular; LC/MS=liquid chromatography/mass spectrometry; LOD=loss on drying; MRM=multiple reaction monitoring; PK=pharmacokinetic; PVP=polyvinylpyrrolidone; SD=standard deviation.

The following examples serve only to illustrate the invention and its practice. The examples are not to be construed as limitations on the scope or spirit of the invention. Raltegravir can be prepared as described in Example 1 of US 2006/0122205 A1. Form 1 crystalline monopotassium salt of raltegravir can be prepared as described in Example 2 of US 2006/0122205 A1.

Reference Example 1

Isentress® Tablets

Isentress® tablets are prepared using the dry granulation procedure described in Example 3 in US 2007/0292504, after which the core tablets are film coated with Opadry II, wherein the Isentress® tablets have the following composition:

| Ingredient[1] | Amount per Tablet (mg) | Amt per batch (wt. percent) |
|---|---|---|
| raltegravir K salt[2] | 434.4 | 50.0 |
| (on free phenol basis) | (400) | (46.0) |
| microcrystalline cellulose IG (AVICEL PH-102) | 169.4 | 19.5 |
| lactose monohydrate IG | 26.06 | 3.0 |
| anhydrous dibasic calcium phosphate IG | 69.5 | 8.0 |
| HPMC IG (Hypromellose 2208) | 43.44 | 5.0 |
| poloxamer 407 IG (micronized grade)[3] | 104.3 | 12.0 |
| sodium stearyl fumarate IG | 8.69 | 1.0 |
| magnesium stearate IG | 8.69 | 1.0 |
| magnesium stearate EG | 4.34 | 0.5 |
| Total: | 868.82 | 100 |
| Opadry II film coating | 26.1 | 3.0 |

[1]IG = intragranular; EG = extragranular.
[2]Form 1 crystalline monopotassium salt of raltegravir; conversion factor = 1.086.
[3]Obtained from BASF. Median particle size = 50 μm.

Example 1

Preparation of Compressed Tablets Containing Raltegravir Potassium and Intragranular and Extragranular Croscarmellose Na (Tablet Ex1)

| Ingredient | Amount per Tablet (mg) | Amt per batch (wt. percent) |
|---|---|---|
| Raltegravir K salt[1, IG] | 434.4 | 62.1 |
| (on free phenol basis) | (400) | (57.1) |
| croscarmellose sodium, IG | 43.4 | 6.2 |
| HPMC 2910 (6 cp), IG | 29.0 | 4.1 |
| microcrystalline cellulose, EG (AVICEL PH-102) | 119.7 | 17.1 |
| croscarmellose sodium, EG | 63.0 | 9.0 |
| magnesium stearate, EG | 10.5 | 1.5 |
| Total | 700 | 100 |

[1]Form 1 crystalline monopotassium salt of raltegravir; conversion factor = 1.086.

Compressed tablets containing 400 mg of raltegravir on a free phenol basis were prepared by first blending a mixture (about 4 kg) of the raltegravir K salt, the HPMC and the intragranular portion of croscarmellose sodium in a Fielder 10/25L high shear granulator at an impeller speed of 500 rpm and a chopper speed of 1800 rpm for 0.5 minute, then adding USP water (40 wt. %; about 1.6 kg) to the granulator and granulating at 250 rpm for 5 minutes at a spray rate of 320 g/minute. The granulated material was then dried in a GPG-3 fluid bed granulator at an inlet air temperature of 80° C. for 20-30 minutes, wherein the air flow rate was initially 200 cubic feet/minute (=5.66 m³/minute) and was gradually reduced during the drying period to a final flow rate of 100 cubic feet/minute (=1.42 m³/minute), to afford a dried granulate with an LOD of about 1 wt. % The dried granulate was then milled and screened using a Quadro 197 Comil with a square bar operated at 2000 rpm fitted with a grated screen having a 1.27 mm opening (i.e., No. 50 screen) to provide the granules which were blended with the microcrystalline cellulose and the extragranular portion of croscarmellose sodium in a 8-quart V-shell blender at an rotation speed of 25 rpm for 5 minutes. Magnesium stearate (pre-screened using a No. 40 mesh size screen) was then added to the blender and the mixture was blended for 5 more minutes at an impeller speed of 25 rpm. The lubricated granules were then compressed into 700 mg tablets using a rotary tablet press with plain oval shaped tooling at a compression force necessary to achieve a tablet hardness of about 15 kiloponds (i.e., 147 Newtons) as measured by using a Key model HT-300 hardness tester. The core tablets were then coated with Opadry II in a Vector film coater (3.75 L pan) to afford film-coated tablets with approximately a 3% weight gain with respect to the core tablet.

Example 2

Preparation of Compressed Tablets Containing Raltegravir Potassium and Intragranular and Extragranular Croscarmellose Na (Tablet Ex2)

| Ingredient | Amount per Tablet (mg) | Amt per batch (wt. percent) |
|---|---|---|
| Raltegravir K salt[1, IG] | 434.4 | 70.03 |
| (on free phenol basis) | (400) | (64.5) |
| croscarmellose sodium, IG | 43.4 | 7 |
| HPMC 2910 (6 cp), IG | 29.0 | 4.67 |
| microcrystalline cellulose & dibasic Ca phosphate, EG (AVICEL DG) | 48.4 | 7.8 |
| croscarmellose sodium, EG | 55.8 | 9.0 |
| magnesium stearate, EG | 9.3 | 1.5 |
| Total | 620.3 | 100 |

[1]Form 1 crystalline monopotassium salt of raltegravir; conversion factor = 1.086.

Preparation.

Compressed tablets containing 400 mg of raltegravir (=64.5% drug loading) and having the ingredients shown in the above table were prepared in accordance with the procedure described in Example 1. These tablets contained the same ingredients as the tablets prepared in Example 1, except that AVICEL DG (7.8 wt. %) replaced AVICEL PH-102 (17.1 wt. %) as the extragranular filler.

Disintegration.

The disintegration times of the Ex1 and Ex2 tablets were obtained in accordance with USP Method <701> using a Vankel VK100 disintegration system (Varian, Inc.), wherein a single tablet was placed in the basket and the basket immersed in a 0.01 N aqueous HCl (deionized water) at 37° C. The time to disappearance of the tablet subsequent to immersion is the disintegration time. The disintegration times (average of two runs for each type of tablet) of the Ex1 and Ex2 tablets were about the same; i.e., about 10 minutes for the Ex1 tablet and about 9 minutes for the Ex2 tablets.

Example 3

Pharmacokinetic Study of Raltegravir Co-Administered with Atazanavir in Healthy Human Males and Females An open-label, 5-period, randomized, crossover study investigating the pharmacokinetics of single oral doses of formulations containing the potassium salt of raltegravir and atazanavir sulfate was conducted in healthy human males and females, with dosing conducted following a light meal. In the first two of the five periods, each subject received in succession a single dose of:

(A) A raltegravir 400 mg tablet prepared substantially in the manner described in Reference Example 1 (i.e., Isentress®), co-administered with Reyataz® (300 mg), and (B) A raltegravir 400 mg tablet prepared substantially in the manner described in Example 1 (i.e., "Tablet Ex1"), coadministered with Reyataz® (300 mg).

Blood samples were taken predose and at 0.5, 1, 1.5, 2, 3, 4, 6, 8, 12, 16, 24, 36, and 48 hours postdose. There was at least a 5-day washout period between each of the doses in treatment arms A, B, C, D, and E starting from the dose administration of the previous period. The safety of the subjects was monitored prior and subsequent to each dosing by clinical evaluation of adverse experiences and by inspection of other safety parameters including blood and urine laboratory safety tests, vital signs, physical examinations, and electrocardiograms.

Sample Preparation and Analysis:

For raltegravir assay, the plasma samples were extracted using 96-well liquid-liquid extraction. Plasma extracts were injected onto an Ace $C_{18}$ (50×3.0 mm, 3 m, titanium rits) HPLC column and analyzed under isocratic conditions with a mobile phase consisting of 42.5/57.5 (v/v %) 0.1 mM EDTA in 0.1% formic acid/methanol, at a flow rate of 0.5 mL/minute. The sample extracts were ionized using an APCI interface and were monitored by MRM in the positive ionization mode. The dynamic range of the LC/MS/MS assay was 2-1000 ng/mL based on a 200 µL aliquot of human plasma.

PK Calculations:

Area under the curve for a plot of plasma concentration v. time to last detectable concentration ($AUC_{0-last}$), was calculated using a non-compartmental model and the Linear Up/Log Down calculation method in WinNonLin Version v5.0.1. AUC values were extrapolated to infinity according to the following equation: $AUC_{0-\infty} = AUC_{0-last} + C_{last}/\beta$, where $C_{last}$ is the last detectable concentration and $\beta$ is the slope of decline of the terminal phase. Observed maximum plasma concentration ($C_{max}$), time of $C_{max}$ ($T_{max}$), and plasma concentration at 12 hr post dosing ($C_{12hr}$) were determined by inspection.

The pharmacokinetic results for raltegravir for doses A and B of the study are as follows

| Treatment Arm | $AUC_{0-\infty}$ (µM · hr) | $AUC_{0-12}$ (µM · hr) | $C_{max}$ (µM) | $C_{12}$ (µM) | $T_{max}$ (hr) | $T_{1/2}$ (hr) |
|---|---|---|---|---|---|---|
| A. Isentress ® (400 mg) + Reyataz ® (300 mg) | 15.5 ± 16.3 | 13.7 ± 14.7 | 4.24 ± 5.40 | 0.305 ± 0.657 | 2.0 (1.0-8.0) | 7.7 ± 6.6 |
| B. Tablet Ex1 (400 mg) + Reyataz ® (300 mg) | 32.9 ± 9.39 | 31.6 ± 9.11 | 10.6 ± 3.86 | 0.177 ± 0.0899 | 2.0 (1.0-4.0) | 8.1 ± 4.9 |

1. The pharmacokinetic values are for raltegravir. The values for $T_{max}$ are the median (min-max); the values for $T_{1/2}$ are the harmonic mean±pseudo standard deviation (SD); and the values for all of the other parameters are the arithmetic mean±SD.
2. The number of subjects n in each treatment protocol was 20.

FIG. 1 is a chart showing the individual and mean AUC values for the dose A and B treatment arms.

Compared to the Isentress® tablets (dose A), the Ex1 tablets (dose B) resulted in increased exposure (i.e., higher AUC values) and notably reduced variability in AUC, $C_{max}$, and $C_{12hr}$. The higher AUC values indicate a potential advantage for efficacy for the Ex1 tablets, and may allow for similar efficacy at a lower dose of raltegravir in tablets employing the formulation of Example 1. The reduced variability can be an advantage as well, leading to more consistent plasma levels of raltegravir.

While the foregoing specification teaches the principles of the present invention, with examples provided for the purpose of illustration, the practice of the invention encompasses all of the usual variations, adaptations and/or modifications that come within the scope of the following claims. All publications, patents, and patent applications cited herein are incorporated by reference herein in their entireties into the disclosure.

What is claimed is:

1. A method for the treatment or prophylaxis of HIV infection or the treatment, prophylaxis or delay in the onset of AIDS in a subject in need thereof which comprises administering to the subject a compressed tablet for oral administration, which comprises:
   (A) an intragranular component comprising:
      (i) an effective amount of the potassium salt of raltegravir,
      (ii) a first superdisintegrant, and
      (iii) a binder; and
   (B) an extragranular component comprising:
      (i) a second superdisintegrant,
      (ii) a filler, and
      (iii) a lubricant;
      with the proviso that the tablet is free of atazanavir or a pharmaceutically acceptable salt thereof,
   wherein:
      (A)(i) the potassium salt of raltegravir is employed on a free phenol basis in an amount of at least about 30 wt. %;
      (A)(ii) the first superdisintegrant is croscarmellose sodium and is employed in an amount in a range of from 3 wt. % to about 12 wt. %;
      (A)(iii) the binder is HPMC and is employed in an amount in a range of from about 0.5 wt. % to about 7 wt. %;
      (B)(i) the second superdisintegrant is croscarmellose sodium and is employed in an amount in a range of from about 3 wt. % to about 20 wt. %;
      (B)(ii) the filler is microcrystalline cellulose and is employed in an amount in a range of from about 10 wt. % to about 40 wt. %; and
      (B)(iii) the lubricant is magnesium stearate and is employed in an amount in a range of from about 0.5 wt. % to about 2.5 wt. %;
      wherein the total amount of superdisintegrant croscarmellose sodium is in a range of from about 6 wt. % to about 20 wt. %; and
      wherein the weight percent of each ingredient in the compressed tablet is based on the total weight of the compressed tablet.

2. The method according to claim 1, wherein the compressed tablet comprises:

(A)(i) the potassium salt of raltegravir is employed in an amount in a range of from about 55 wt. % to about 60 wt. % on a free phenol basis;
(A)(ii) the intragranular first superdisintegrant is croscarmellose sodium and is employed in an amount in a range of from about 5 wt. % to about 7 wt. %;
(A)(iii) the binder is HPMC and is employed in an amount in a range of from about 3 wt. % to about 5 wt. %;
(B)(i) the extragranular second superdisintegrant is croscarmellose sodium and is employed in an amount in a range of from about 8 wt. % to about 10 wt. %;
(B)(ii) the filler is microcrystalline cellulose and is employed in an amount in a range of from about 16 wt. % to about 18 wt. %; and
(B)(iii) the lubricant is magnesium stearate and is employed in an amount in a range of from about 1 wt. % to about 2 wt. %;
wherein the total amount of croscarmellose sodium is in a range of from about 13 wt. % to about 17 wt. %.

3. The method according to claim 1, wherein the compressed tablet comprises:
(A)(i) the potassium salt of raltegravir is employed in an amount in a range of from about 55 wt. % to about 65 wt. % on a free phenol basis;
(A)(ii) the intragranular first superdisintegrant is croscarmellose sodium and is employed in an amount in a range of from about 5 wt. % to about 8 wt. %;
(A)(iii) the binder is HPMC and is employed in an amount in a range of from about 3 wt. % to about 5 wt. %;
(B)(i) the extragranular second superdisintegrant is croscarmellose sodium and is employed in an amount in a range of from about 8 wt. % to about 10 wt. %;
(B)(ii) the filler is a combination of microcrystalline cellulose and dibasic calcium phosphate and is employed in an amount in a range of from about 7 wt. % to about 10 wt. %; and
(B)(iii) the lubricant is magnesium stearate and is employed in an amount in a range of from about 1 wt. % to about 2 wt. %;
wherein the total amount of croscarmellose sodium is in a range of from about 13 wt. % to about 17 wt. %.

4. The method according to claim 1 wherein, in the compressed tablet, the potassium salt of raltegravir is Form 1 crystalline potassium salt of raltegravir.

5. The method according to claim 2 wherein, in the compressed tablet, the potassium salt of raltegravir is Form 1 crystalline potassium salt of raltegravir.

6. The method according to claim 3 wherein, in the compressed tablet, the potassium salt of raltegravir is Form 1 crystalline potassium salt of raltegravir.

7. The method according to claim 1, wherein, in the compressed tablet, the potassium salt of raltegravir is employed on a free phenol basis in an amount in a range of from about 200 mg to about 600 mg per unit dose.

8. The method according to claim 2 wherein, in the compressed tablet, the potassium salt of raltegravir is employed on a free phenol basis in an amount in a range of from about 200 mg to about 600 mg per unit dose.

9. The method according to claim 3 wherein, in the compressed tablet, the potassium salt of raltegravir is employed on a free phenol basis in an amount in a range of from about 200 mg to about 600 mg per unit dose.

10. The method according to claim 7 wherein, in the compressed tablet, the potassium salt of raltegravir is employed on a free phenol basis in an amount of about 600 mg per unit dose.

11. The method according to claim 1, wherein one or more of said tablets are administered once daily.

12. The method according to claim 10, wherein the one or more of said tablets are administered at or about the same time.

13. The method according to claim 2, wherein the compressed tablet has the following composition:

| Ingredient | Relative Amount (wt. %) |
| --- | --- |
| raltegravir K salt | 62.1 (57.1 on free phenol basis) |
| croscarmellose Na (intragranular) | 6.2 |
| HPMC2910 (6 cp) | 4.1 |
| microcrystalline cellulose, having a nominal particle size of about 100 μm, a moisture content of about 3% to about 5%, and a loose bulk density of from about 0.26 to about 0.31 g/cc | 17.1 |
| croscarmellose Na (extragranular) | 9.0 |
| Mg stearate | 1.5 |
| Total | 100. |

14. The method according to claim 2, wherein the compressed tablet has the following composition:

| Ingredient | Relative Amount (wt. %) | Unit Dosage Amount (mg) |
| --- | --- | --- |
| raltegravir K salt | 62.1 (57.1 on free phenol basis) | 434.4 (= 400 mg free phenol) |
| croscarmellose Na (intragranular) | 6.2 | 43.4 |
| HPMC2910 (6 cp) | 4.1 | 29.0 |
| microcrystalline cellulose, having a nominal particle size of about 100 μm, a moisture content of about 3% to about 5%, and a loose bulk density of from about 0.26 to about 0.31 g/cc | 17.1 | 119.7 |
| croscarmellose Na (extragranular) | 9.0 | 63.0 |
| Mg stearate | 1.5 | 10.5 |
| Total | 100 | 700. |

15. The method according to claim 13 wherein, in the compressed tablet, the potassium salt of raltegravir is Form 1 crystalline potassium salt of raltegravir.

16. The method according to claim 14 wherein, in the compressed tablet, the potassium salt of raltegravir is Form 1 crystalline potassium salt of raltegravir.

* * * * *